United States Patent [19]

Patterson

[11] Patent Number: 4,594,133

[45] Date of Patent: Jun. 10, 1986

[54] PROCESS FOR PREPARING 3'-HALODIPHENYLETHERS

[75] Inventor: Dennis R. Patterson, North Wales, Pa.

[73] Assignee: Rohm and Haas Company, Philadelphia, Pa.

[21] Appl. No.: 776,195

[22] Filed: Sep. 16, 1985

[51] Int. Cl.$^4$ .............................................. B01J 11/12
[52] U.S. Cl. ................................................... 204/158.1
[58] Field of Search ................................. 204/158 HA

[56] References Cited

U.S. PATENT DOCUMENTS

| | | | |
|---|---|---|---|
| 3,950,435 | 4/1976 | Takahashi et al. | 260/613 R |
| 3,966,453 | 6/1976 | Takahashi et al. | 71/105 |
| 4,046,798 | 9/1977 | Bayer et al. | 260/465 D |
| 4,093,446 | 6/1978 | Bayer et al. | 71/109 |
| 4,252,624 | 2/1981 | Stephan | 204/158 HA |
| 4,358,308 | 11/1982 | Swithenbank | 71/98 |
| 4,419,122 | 12/1983 | Swithenbank | 71/98 |
| 4,485,254 | 11/1984 | Tanger | 560/21 |

FOREIGN PATENT DOCUMENTS 1079303  6/1980  Canada ............................ 204/613 R

OTHER PUBLICATIONS

Wilson, "The Reaction of Halogens with Silver Salts of Carboxylic Acids", *Organic Reactions*, vol. IX, Chapter 5, pp. 333–387 (1957).
Sosnovsky, "Reactions of Halogens with Salts of Carboxylic Acids", *Free Radical Reactions in Preparative Organic Chemistry*, pp. 383–386 (1964).
Larock, "Organomercurials as Reagents and Intermediates in Organic Synthesis", *New Applications of Organometallic Reagents in Organic Synthesis*, pp. 257, 264, 265, (1976).
Bamford and Tipper, "Halogenolysis (Halogenodemetallation) of Organometallic Compounds", *Chemical Kinetics*, vol. 12, pp. 135–176 (1973).
Makarova, "Reaction of Organomercury Compounds, Part 2", *Organometallic Reactions*, pp. 411–421 (1971).
Meyers and Fleming, 44, *J. Org. Chem.*, 3405 (1979).
Kochi, "Metal Complexes in Organic Oxidations", *Organometallic Mechanisms and Catalysis*, pp. 99–103 (1978).
Silbert, 46, *J. Am. Oil Chemists Soc.*, 615 (1969).
Buchler and Pearson, "Survey of Organic Synthesis", pp. 352–353 (1970).
Buchler and Pearson, "Survey of Organic Synthesis", vol. 2, pp. 354–355 (1977).

*Primary Examiner*—Howard S. Williams
*Attorney, Agent, or Firm*—John C. Demeter

[57] ABSTRACT

This process relates to the halodecarboxylation of 3'-carboxydiphenylethers utilizing mercuric oxide, molecular halogen, and light in an inert atmosphere at moderate temperatures and at atmospheric pressure to afford 3'-halodiphenylethers.

8 Claims, No Drawings

PROCESS FOR PREPARING 3'-HALODIPHENYLETHERS

BACKGROUND OF THE INVENTION

This invention relates to a process for the preparation of 3'-halodiphenylethers.

The preparation of certain diphenylethers is generally reported in the literature to be accomplished by reacting a suitably substituted phenol or alkali metal salt thereof with a suitably substituted halobenzene in the presence of an alkaline agent in a polar aprotic solvent and optionally including a catalyst. See, for example, U.S. Pat. Nos. 3,966,453; 3,950,435; 4,046,789; 4,093,446; 4,358,308 and Canadian Pat. No. 1,079,303.

Diphenylethers prepared by the above techniques are also generally reported in the literature to be used as precursors in preparing certain other diphenylether derivatives. For example, the 4'-halo or 4'-nitro derivatives are prepared by halogenating or nitrating an otherwise suitably substituted diphenylether. Further, 3'-hydroxydiphenylethers can be converted to alpha-oxymethylene carboxylic esters by condensation with alpha-halo esters in the presence of bases such as potassium carbonate or hydroxide. These alpha-oxymethylene carboxylic esters can then be converted to the corresponding carboxylic acids, acid chlorides or amides. Still further, 3'-alkoxydiphenylethers can be made by reacting the corresponding 3'-halodiphenylethers prepared by the above described techniques with a carbinol in an inert nonpolar solvent in the presence of base.

SUMMARY OF THE INVENTION

This invention relates to a process for the preparation of 3'-halodiphenylethers having the formula

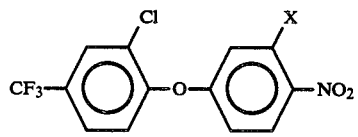

wherein X is halo (bromo or iodo) which comprises halodecarboxylation of a diphenylether having the formula

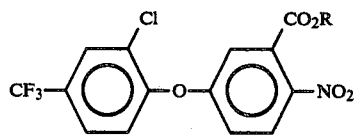

where R is hydrogen or an alkali metal or alkaline earth metal salt thereof, in a nonpolar solvent in the presence of mercuric oxide (HgO), molecular halogen (Br$_2$ or I$_2$) and light in a substantially inert atmosphere at about atmospheric pressure and temperatures from about 65° C. to about 150° C.

DETAILED DESCRIPTION OF THE INVENTION

This invention relates to a process utilizing about atmospheric pressure, a substantially inert atmosphere, moderate temperatures, light, molecular halogen and mercuric oxide for the halodecarboxylation of certain 3'-carboxydiphenylether. Unless otherwise stated, "equivalents" means on a molar basis. In particular, this invention relates to the preparation of 3'-halodiphenylethers having the formula

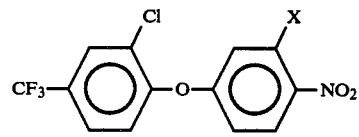

wherein X is bromo or iodo which comprises halodecarboxylation of a diphenylether having the formula

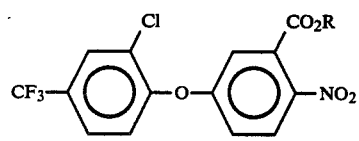

wherein R is hydrogen or alkali metal or alkaline earth metal salt thereof, in a nonpolar solvent in the presence of mercuric oxide (HgO), molecular halogen (Br$_2$ or I$_2$), at least about 25 watts of light, at temperatures from about 65° C. to about 150° C., in a substantially inert atmosphere and about atmospheric pressure.

In the above process, typical nonpolar solvents that can be utilized include alkanes such as hexane or cyclohexane, aromatics such as benzene or toluene, or halogenated hydrocarbons such as carbon tetrachloride or methylene chloride. Carbon tetrachloride is the preferred solvent.

Generally from about 0.5 to about 5 equivalents of mercuric oxide is used per equivalent of substrate (Formula II). Preferably, about 1 equivalent of mercuric oxide is utilized per equivalent of substrate (Formula II).

The amount of molecular halogen (Br$_2$ or I$_2$) utilized generally is from about 1 to about 5 equivalents for each equivalent of substrate (Formula II). Preferably, about 1.5 equivalents of molecular halogen is utilized per equivalent of substrate (Formula II).

The presence of a source of light is also needed in this process. The light should have a power rating of at least about 25-watts and preferably at least about 75-watts.

Temperatures utilized for the process of this invention are from about 65° C. to about 150° C., preferably from about 75° C. to about 110° C.

The process of the present invention should be carried out in a substantially inert atmosphere such as nitrogen or argon.

The reagents used in this halodecarboxylation process can be combined in any order.

The 3'-carboxylic acid, alkali salt or alkaline earth metal salt diphenylether of Formula II can be prepared by standard techniques known in the art such as those described in the Background of the Invention section above or by the process disclosed in U.S. Pat. No. 4,485,254 which is incorporated herein by reference.

The alkali metal salts such as sodium, potassium, lithium and the like, and the alkaline earth metal salts such as magnesium, calcium and the like, of the carboxylic acids of Formula II are prepared by treating the carboxylic acid with an alkali metal hydroxide or hydride, or an alkaline earth metal hydroxide or hydride such as sodium hydroxide, potassium hydroxide, calcium hydroxide, sodium hydride, magnesium hydride and the like in an inert or substantially inert solvent.

The 3'-halodiphenylethers prepared by the process of this invention can be used as herbicides or as intermediates in the preparation of other herbicidal diphenylethers by techniques known to those skilled in the art.

The following examples are presented to further illustrate the process of this invention and are not intended to limit the breadth and scope of the invention in any way.

EXAMPLE 1

Preparation of 2-chloro-4-trifluoromethyl-3'-bromo-4'-nitrodiphenylether

A 50 ml, 3-necked flask was fitted with stir bar, thermometer and reflux condenser. A nitrogen inlet was attached to the condenser and the flask was flushed with nitrogen. 2-Chloro-4-triflluoromethyl-3'-carboxy-4'-nitrodiphenylether (3.62 g, 0.01 mol) was slurried in carbon tetrachloride (25 ml) and the mercuric oxide (red, 3.26 g, 0.01 mol) was added in one portion. The equipment was wrapped in aluminum foil and the mixture was gently refluxed. Bromine (2.40 g, 0.015 mol) was dissolved in carbon tetrachloride (5 ml) and added directly to the mixture. A portion of the foil was opened to allow a 100-watt light bulb to shine into the reaction mixture. The reflux was continued for 3 hours. At this time, the irradiation was stopped and the heat source (heating mantle) was removed. The crude product was allowed to cool to room temperature. Water, and then saturated aqueous sodium bicarbonate were added and the mixture was stirred for 20 min. The mixture was vacuum filtered and the layers were separated. The organic layer was concentrated under vacuum to provide an oil containing some white solid. Thin-layer chromatography of this oil on silica gel using 2/98 v/v $C_2Cl_2$/hexane showed two major components of Rf's 0.5 and 0.8. Neither component corresponded to starting material. Treatment of the product oil with 5 ml methylene chloride gave precipitation of a white solid. The mixture was vacuum filtered to provide white needles (1.2 g, the Rf=0.5 component). The mother liquor was concentrated under vacuum to give a yellow oil (1.8 g, nearly pure $R_f$=0.5 component). This oil was identified as the 3'-bromo product by comparison of its proton nuclear magnetic resonance ($^1$H-NMR) spectrum with that of the 2-chloro-4-trifluoromethyl-3'-carboxy-4-nitro-diphenylether starting material.

EXAMPLE 2

Preparation of 2-chloro-4-trifluoromethyl-3'-bromo-4'-nitrodiphenylether

The procedure in Example 1 was substantially followed on a 10X scale to provide the semi-pure $R_f$=0.8 component as an oily yellow-brown solid (17 g, 46% crude yield based on 2-chloro-4-trifluoromethyl-3'-carboxy-4'-nitrodiphenylether starting material). A portion of this product (5 g) was chromatographed on a 2" diameter, 12" length column containing 70-320 mesh silica gel. The column was eluted with 5/95 v/v EtOAc/hexane, increasing to 10/90 v/v EtOAc/hexane. From this treatment, a tan solid (3 g, pure, corresponds to 26% yield from 2-chloro-4-trifluoromethyl-3'-carboxy-4'-nitrodiphenylether, m.p. 52°-54° C.) was obtained. The combustion analysis of this product corresponded to 3'-bromo-2-chloro-4'-nitro-4-trifluoromethyl diphenylether, $C_{13}H_6BrClF_3NO_3$.

| Element | Expected (%) | Found (%) |
| --- | --- | --- |
| C | 39.38 | 39.22 |
| H | 1.52 | 1.62 |
| Br | 20.15 | 19.80 |
| Cl | 8.95 | 9.08 |
| F | 14.37 | 14.55 |
| N | 3.53 | 3.66 |
| Hg | 0.00 | 0.75 |
| (O) | (12.10) | (11.32) |
| | 100.00 | (100.00) |

EXAMPLE 3

Preparation of 2-chloro-4-trifluoromethyl-3'-iodo-4'-nitrodiphenylether

2-Chloro-4-trifluoromethyl-3'-carboxy-4'-nitrodiphenylether (10 g), red mercuric oxide (9 g) and iodine (10 g) were reacted in carbon tetrachloride at 77° C. under nitrogen with irradiation, as described in Example 1. The workup of this reaction included addition of 5% aqueous sodium bisulfite solution prior to addition of sodium bicarbonate solution. Chromatography as described in Example 2 provided yellow crystals (1.90 g, 16% yield based on 2-chloro-4-trifluoromethyl-3'-carboxy-4'-nitrodiphenylether, m.p. 71°-73° C.). The combustion analysis of this product corresponded to 2-chloro-3'-iodo-4'-nitro-4-trifluoromethyldiphenylether, $C_{13}H_6ClF_3INO_3$.

| Element | Calculated (%) | Found (%) |
| --- | --- | --- |
| C | 35.20 | 36.35 |
| H | 1.36 | 1.65 |
| Cl | 7.99 | 9.21 |
| F | 12.85 | 12.71 |
| I | 28.61 | 27.63 |
| N | 3.16 | 3.11 |
| (O) | 10.82 | (9.34) |
| | 100.00 | (100.00) |

What is claimed is:

1. A process for preparing a compound having the formula:

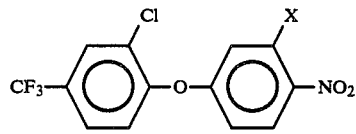

wherein X is bromo or iodo which comprises reacting a diphenylether having the formula:

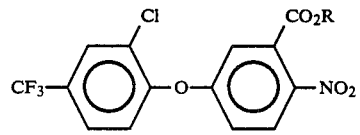

where R is hydrogen or an alkali metal or alkaline earth metal salt thereof, with mercuric oxide and molecular bromine or iodine in a nonpolar solvent at about atmospheric pressure in a substantially inert atmosphere, in the presence of light at temperatures from about 65° C. to about 150° C.

2. The process of claim 1 wherein from about 0.5 to about 5 equivalents of mercuric oxide is used per equivalent of diphenylether having the formula

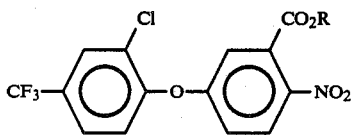

where R is hydrogen or an alkali metal or alkaline earth metal salt thereof.

3. The process of claim 2 wherein about one equivalent of mercuric oxide is used per equivalent of said diphenylether.

4. The process of claim 1 wherein from about 1 to about 5 equivalents of molecular bromine or iodine is used for each equivalent of diphenylether having the formula

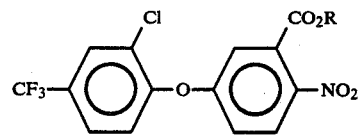

where R is hydrogen or an alkali metal or alkaline earth metal salt thereof.

5. The process of claim 4 wherein about 1.5 equivalents of molecular bromine or iodine is utilized per equivalent of said diphenylether.

6. The process of claim 1 wherein at least about 25-watts of light is used.

7. The process of claim 6 wherein at least about 75-watts of light is used.

8. The process of claim 1 wherein the reaction is carried out at temperature between about 75° C. and about 110° C.

* * * * *